US010398603B2

(12) United States Patent
Locke et al.

(10) Patent No.: US 10,398,603 B2
(45) Date of Patent: Sep. 3, 2019

(54) REDUCED-PRESSURE, WOUND-TREATMENT DRESSINGS AND SYSTEMS

(71) Applicant: KCI Licensing, Inc., San Antonio, TX (US)

(72) Inventors: Christopher Brian Locke, Bournemouth (GB); Timothy Mark Robinson, Basingstoke (GB)

(73) Assignee: KCI Licensing, Inc., San Antonio, TX (US)

( * ) Notice: Subject to any disclaimer, the term of this patent is extended or adjusted under 35 U.S.C. 154(b) by 1186 days.

(21) Appl. No.: 13/894,217

(22) Filed: May 14, 2013

(65) Prior Publication Data
US 2013/0253401 A1    Sep. 26, 2013

Related U.S. Application Data

(62) Division of application No. 12/610,910, filed on Nov. 2, 2009, now Pat. No. 8,460,257.
(Continued)

(51) Int. Cl.
*A61F 13/00* (2006.01)
*A61M 1/00* (2006.01)
(Continued)

(52) U.S. Cl.
CPC ...... *A61F 13/00068* (2013.01); *A61B 17/085* (2013.01); *A61F 13/00987* (2013.01); *A61M 1/0088* (2013.01); *A61B 2017/00526* (2013.01); *A61B 2017/00867* (2013.01); *A61B 2017/00884* (2013.01); *A61B 2017/00889* (2013.01);
(Continued)

(58) Field of Classification Search
CPC .......... A61F 13/00; A61F 13/02; A61F 5/44; A61M 1/00; A61M 27/00
USPC .......... 604/35, 305–308, 313, 317–323, 403, 604/406, 540–544, 902; 606/131
See application file for complete search history.

(56) References Cited

U.S. PATENT DOCUMENTS

| 1,355,846 A | 10/1920 | Rannells |
| 2,012,755 A | 8/1935 | De Muth |

(Continued)

FOREIGN PATENT DOCUMENTS

| AU | 550575 A1 | 3/1986 |
| AU | 745271 | 4/1999 |

(Continued)

OTHER PUBLICATIONS

Collins English Dictionary—Complete and Unabridged © HarperCollins Publishers 1991, 1994, 1998, 2000, 2003.*
(Continued)

*Primary Examiner* — Tatyana Zalukaeva
*Assistant Examiner* — Ilya Y Treyger

(57) ABSTRACT

A wound-closing dressing, which is suitable for use as part of a reduced-pressure, wound-treatment system, may include a sealing drape, one or more contracting elements, and a gripping member. The contracting element may be coupled to the sealing drape and is configured to contract when activated and to generate a closing force. A gripping member is coupled to the sealing drape and is configured to transmit the closing force to a patient's epidermis. Other dressings, systems, and methods are also disclosed.

16 Claims, 9 Drawing Sheets

Related U.S. Application Data

(60) Provisional application No. 61/112,371, filed on Nov. 7, 2008.

(51) Int. Cl.
  *A61B 17/08* (2006.01)
  *A61F 13/02* (2006.01)
  *A61F 5/44* (2006.01)
  *A61M 27/00* (2006.01)
  *A61B 17/00* (2006.01)
  *A61B 17/34* (2006.01)

(52) U.S. Cl.
  CPC .............. *A61B 2017/00893* (2013.01); *A61B 2017/086* (2013.01); *A61B 2017/345* (2013.01); *A61M 2205/0266* (2013.01); *Y10T 29/49826* (2015.01)

(56) References Cited

U.S. PATENT DOCUMENTS

| | | | |
|---|---|---|---|
| 2,547,758 A | 4/1951 | Keeling | |
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,709,021 B2 * | 5/2010 | Serafica .................. A61L 15/28 424/443 |
| 8,834,434 B2 | 9/2014 | Hu et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2003/0023196 A1 | 1/2003 | Liguori | |
| 2004/0161453 A1 | 8/2004 | Serafica et al. | |
| 2008/0033334 A1 | 2/2008 | Gurtner et al. | |
| 2010/0049151 A1 | 2/2010 | Aicher | |
| 2010/0057025 A1 | 3/2010 | Aicher | |

FOREIGN PATENT DOCUMENTS

| | | |
|---|---|---|
| AU | 755496 | 2/2002 |
| CA | 2005436 | 6/1990 |
| CA | 2669039 A1 | 6/2008 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |

(56) References Cited

FOREIGN PATENT DOCUMENTS

| WO | 80/02182 | 10/1980 |
|---|---|---|
| WO | 87/04626 | 8/1987 |
| WO | 90/010424 | 9/1990 |
| WO | 93/09727 | 5/1993 |
| WO | 94/020041 | 9/1994 |
| WO | 96/05873 | 2/1996 |
| WO | 97/18007 | 5/1997 |
| WO | 99/13793 | 3/1999 |
| WO | WO2005105174 A1 | 10/2005 |
| WO | 2008039839 A2 | 4/2008 |
| WO | 2008100437 | 8/2008 |
| WO | 2008103406 | 8/2008 |

OTHER PUBLICATIONS

Decision of Rejection dated Jul. 31, 2014, Japanese Application No. 2011-534856.
CA2742962 in connection with Office Action dated Aug. 25, 2016.
European Search Report corresponding to EP09825282.8, dated May 18, 2017.
N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).
Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).

\* cited by examiner

US 10,398,603 B2

REDUCED-PRESSURE, WOUND-TREATMENT DRESSINGS AND SYSTEMS

RELATED APPLICATIONS

This application is a Divisional of U.S. application Ser. No. 12/610,910 filed Nov. 2, 2009, which claims the benefit, under 35 U.S.C § 119(e), of the filing of U.S. Provisional Patent Application Ser. No. 61/112,371, entitled "Reduced-Pressure Wound Treatment Dressing and System," filed Nov. 7, 2008, which is incorporated herein by reference for all purposes.

BACKGROUND

The present invention relates generally to medical treatment systems, and more particularly, to a reduced-pressure, wound-treatment dressings, systems, and methods.

Wounds may be received either intentionally, such as surgical incisions, or unintentionally, such as in an accident. In either case, closure of the wound is important to prevent loss of vital body fluids and invasion by micro-organisms. Wounds are typically closed through the use of sutures or staples.

The use of sutures or staples may, however, have undesirable side-effects. For example, the insertion of sutures or staples necessarily involves inflicting the patient with an additional wound where the sutures or staples enter the epidermis of the patient. These additional wounds are also subject to possible infection. Moreover, while the wound itself may result in scarring, the additional wounds from the sutures or staples may also result in additional scarring, which may unnecessarily highlight the already atheistically undesirable nature of the original wound scar.

BRIEF SUMMARY

Shortcomings with wound care are addressed by the present invention as shown and described in a variety of illustrative, non-limiting embodiments herein. According to an illustrative, non-limiting embodiment, a reduced-pressure, wound-treatment system for treating a wound on a patient includes a wound-closing dressing, a manifold member for disposing between a tissue-facing surface of a sealing drape and the wound; and a reduced-pressure subsystem for delivering a reduced pressure to the wound-closing dressing. The wound-closing dressing includes the sealing drape having a first surface and a tissue-facing surface, a contracting element coupled to the sealing drape, and a gripping member coupled to the sealing drape. The sealing drape is for placing over the wound. The contracting element is configured to contract when activated and to thereby generate a closing force. The gripping member is configured to transmit the closing force to a patient's epidermis. The sealing drape and gripping member are configured to form a fluid seal over the wound.

According to another illustrative, non-limiting embodiment, a wound-closing dressing includes a sealing drape having a first surface and a tissue-facing surface, a contracting element coupled to the sealing drape, and a gripping member coupled to the sealing drape. The sealing drape is for placing over the wound. The contracting element is configured to contract when activated and to thereby generate a closing force. The gripping member is configured to transmit the closing force to a patient's epidermis. The sealing drape and gripping member are configured to form a fluid seal over the wound.

According to another illustrative, non-limiting embodiment, a wound-closing dressing includes a sealing drape having a first surface and a tissue-facing surface, a dissolvable body coupled to the sealing drape, and an elastic member coupled to the dissolvable body in a stretched position. The sealing drape is for placing over a wound. The elastic member contracts to a free position when at least a portion of the dissolvable body dissolves thereby generating a closing force. The wound-closing dressing further includes a gripping member coupled tout least one of the sealing drape and elastic member. The gripping member is configured to transmit the closing force to a patient's epidermis.

According to another illustrative, non-limiting embodiment, a method for treating a wound includes the steps of securing a contracting element to a patient's epidermis such that the contracting element spans at least a portion of the patient's wound and activating the contracting element such that the contracting element generates a closing force. The contracting element is configured to contract from an extended position to a contracted position and thereby generates the closing force when activated.

According to another illustrative, non-limiting embodiment, a method of manufacturing a wound closing dressing includes the steps of forming a sealing drape having a first surface and a tissue-facing surface, coupling a contracting element to the sealing drape, and coupling a gripping member to the sealing drape. The gripping member is configured to transmit the closing force to a patient's epidermis. The contracting element is configured to contract from an extended position to a contracted position and thereby generates a closing force when activated.

BRIEF DESCRIPTION OF THE DRAWINGS

A more complete understanding of the present invention may be obtained by reference to the following Detailed Description when taken in conjunction with the accompanying Drawings wherein.

DETAILED DESCRIPTION

Figure 1:
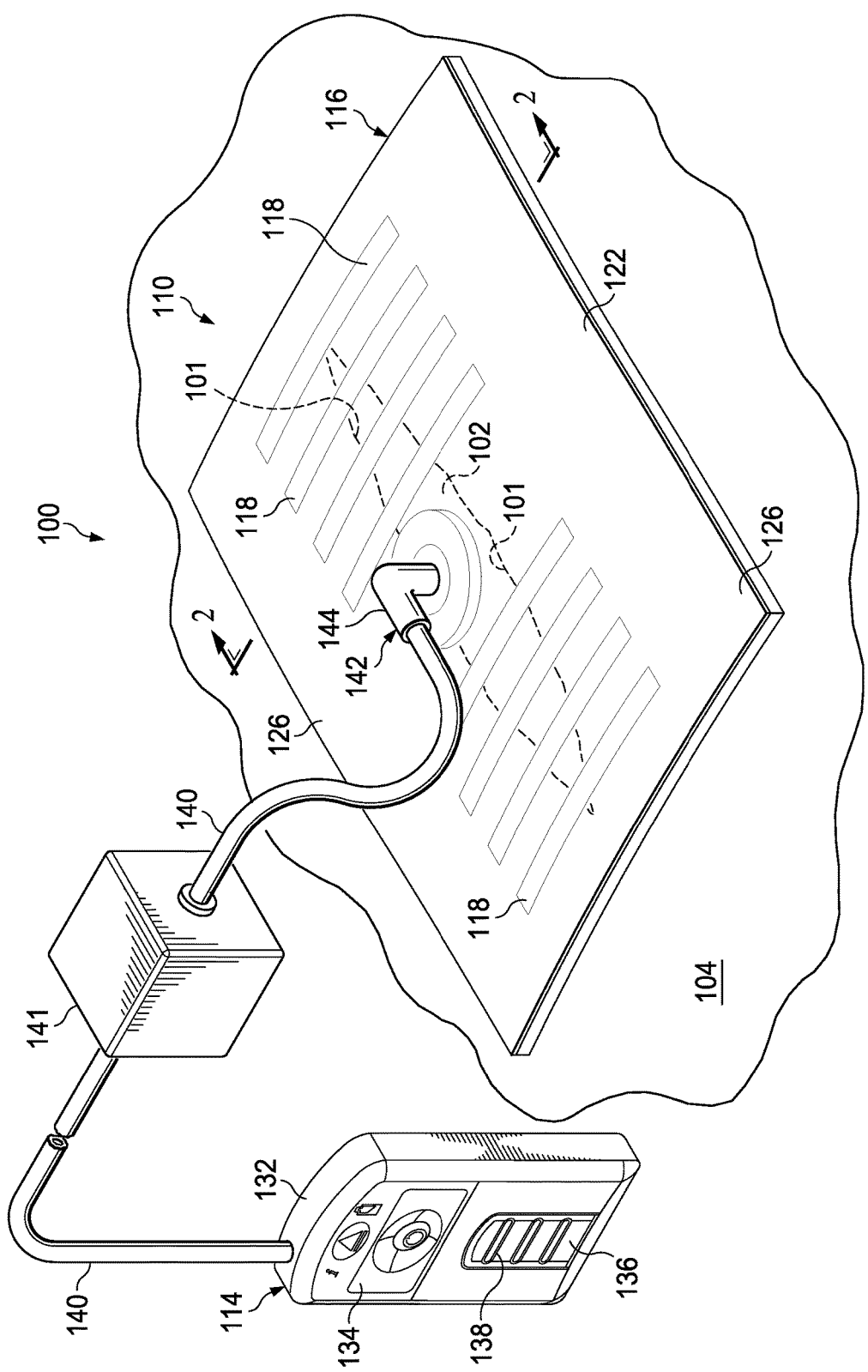
FIG. 1 is a schematic, perspective view of an illustrative, non-limiting embodiment of a system for treating a wound on a patient.
Figure 2:
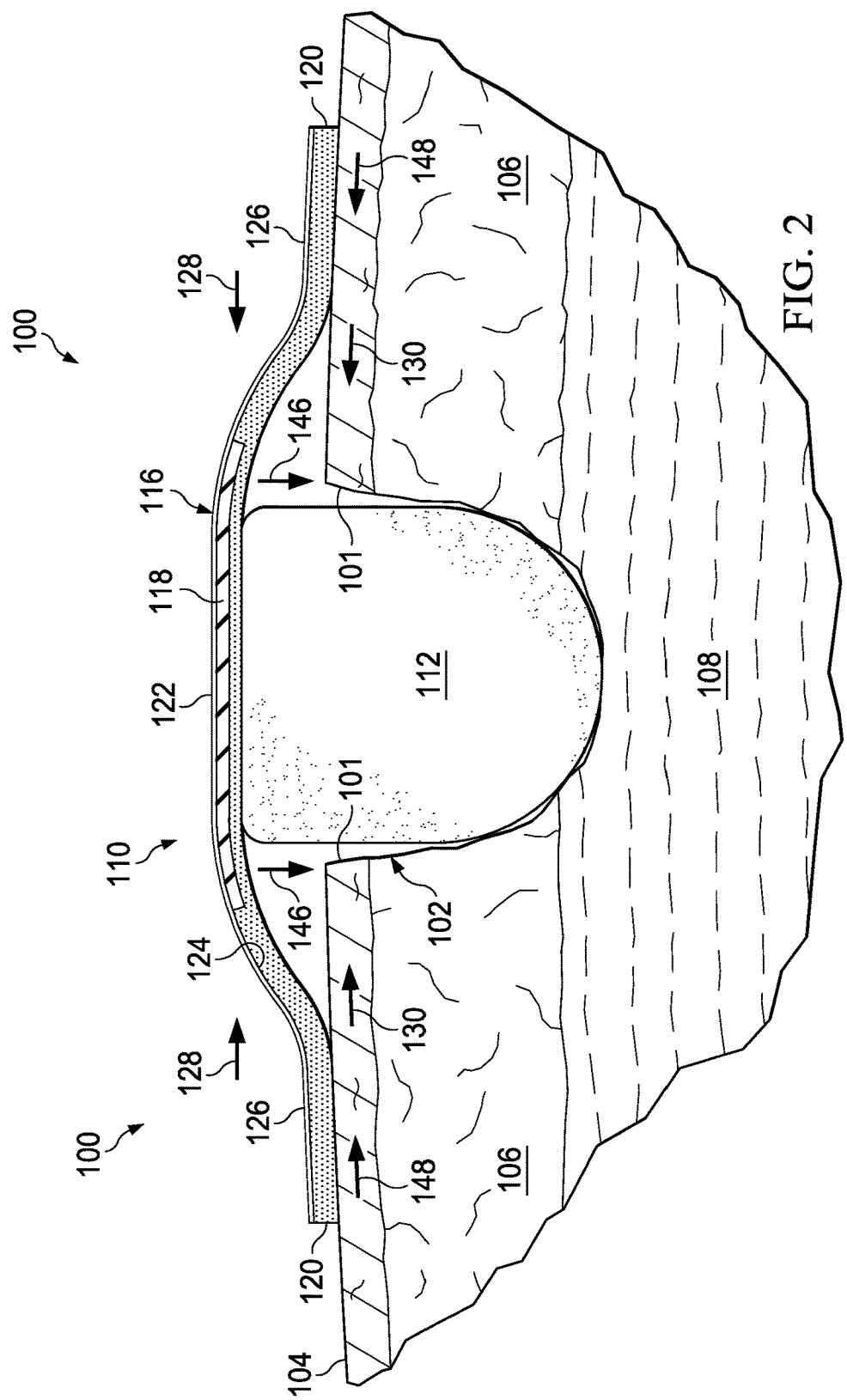
FIG. 2 is a schematic, cross-sectional view of the system of FIG. 1 taken along line 2-2 in FIG. 1.

In the following detailed description of the preferred embodiments, reference is made to the accompanying drawings that form a part hereof, and in which is shown, by way of illustration, specific embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

Referring now primarily to FIGS. 1-3B, a first illustrative, non-limiting embodiment of a reduced-pressure, wound-treatment system 100 for treating a wound 102 on a patient is shown. The reduced-pressure, wound-treatment system 100 generally includes a wound-closing dressing 110, a manifold member 112, and a reduced-pressure subsystem 114. The reduced-pressure, wound-treatment system 100 is shown in a region around the wound 102. In this illustration, the wound 102 is through epidermis 104 (or skin), dermis 106, and reaches into a hypodermis, or subcutaneous tissue 108. The subcutaneous tissue 108 may include numerous tissue types, such as fatty tissue or muscle. While the wound 102 in the illustrative embodiment is shown as reaching through the epidermis 104, dermis 106 and into the subcutaneous tissue 108, it will be appreciated that the reduced-pressure, wound-treatment system 100 may be used to treat a wound of any depth.

The wound-closing dressing 110 includes a sealing drape 116, one or more contracting elements 118, and a gripping member 120. The sealing drape 116 includes a first surface 122 and a second, tissue-facing surface 124. The sealing drape 116 may be sized so that the sealing drape 116 overlaps the wound 102 in such a manner that drape extensions 126 extend beyond a periphery of the wound 102.

The sealing drape 116 may be an elastomeric material. "Elastomeric" means having the properties of an elastomer. It generally refers to a polymeric material that has rubber-like properties. More specifically, most elastomers have elongation rates greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Additional, specific examples of sealing member materials include a silicone drape, 3M Tegaderm® drape, acrylic drape such as one available from Avery Dennison, or an incise drape material. However, it will be appreciated that the sealing drape 116 may be formed from any suitable material. In one alternative, the sealing drape 116 may be fenestrated to allow moisture or water vapor to pass through in order to activate the contracting elements (discussed further below). Unless otherwise indicated, as used herein, "or" does not require mutual exclusivity.

One or more contracting elements 118 are coupled to the sealing drape 116. Each contracting element 118 is configured to contract when activated in order to generate a closing force (such as in the direction illustrated by vectors or arrows 128 in FIG. 3B) that may assist in closing the wound 102. In the illustrative embodiment, the contracting elements 118 are in a stretched position when the wound-closing dressing 110 is applied to the patient. The contracting elements 118 may be coupled to the sealing drape 116 in a stretched position or may be moved to a stretched position as the wound-closing dressing 110 is being applied to the patient. In either case, when the contracting elements 118 are activated, they seek to return to a non-stretched, or free position, and thereby contract to generate a closing force. Other illustrative ways of contracting are described further below.

The wound-closing dressing 110 may include a variety of contracting elements 118 arranged in numerous configurations. For example, as shown in FIGS. 1-3B, the wound-closing dressing 110 may include a plurality of contracting elements 118 that are each formed as a strip. Alternatively, the wound-closing dressing 110 may include a single contracting element 118. In yet another embodiment, one or more contracting elements 118 may be woven into the sealing drape 116 or woven into an additional member, such as gauze, another drape-like piece, etc., which is coupled to the sealing drape 116. Additionally, each contracting element 118 may be coupled to the sealing drape 116 by any suitable device or technique, including, but not limited to, welding (e.g., ultrasonic or RF welding), bonding, mechanical fasteners, adhesives, cements, etc. Alternatively, each contracting element 118 may be molded into the sealing drape 116. The contracting elements 118 are coupled to the second, tissue-facing surface 124 of the sealing drape 116 or to the first surface 122 of the sealing drape 116 or an internal portion of the sealing drape 116.

Each contracting element 118 may be formed from any suitable material that contracts in response to being activated. The contracting element 118 is configured to move from an extended position to a contracted position (or free position) upon full activation. For example, each contracting element 118 may be formed from cellulose whereby moisture causes the contracting element 118 to contract. The moisture may be introduced from the patient's own exudate. Alternatively or in addition, the moisture, by way of a fluid, such as water, bacteriostatic water, saline, etc., may be introduced to the wound 102 or wound area prior to the wound-closing dressing 110 being applied to the patient. In yet another alternative or addition, the sealing drape 116 may be provided with a port (not shown) for introducing fluid to the wound area to activate the contracting elements 118 after the wound-closing dressing 110 has been applied to the patient.

In another alternative or addition, the contracting elements 118 may be formed from a shape-memory metal that contracts in response to being activated. One example of a suitable shape-memory metal is Nitinol material from Nitinol Devices & Components of Fremont, Calif. The contracting elements 118 formed from a shape-memory metal may be activated by heat, such as a patient's body heat, warming pads, heat lamps, etc. Alternatively or in addition, the contracting elements 118 may be activated by the introduction of electromagnetic induction. It will, however, be appreciated that the contracting elements 118 may be formed from any suitable material, including but not limited to shape memory alloys, magnetic shape memory alloys, shape memory polymers, piezoelectric materials, electroactive polymers, magnetorheological fluids and elastomers, and electrorheological fluids. Depending on the particular material, the activation may take the form of an electric field, a temperature change, a magnetic field, a mechanical loading or stressing, light, UV-light, changes in environmental pH, ultrasound, moisture, etc.

The gripping member 120 facilitates transmission of closing force (shown by arrows 128) generated by the contraction of the contracting elements 118 to the patient's skin. The transmitted force is illustrated as force vectors 130 in FIG. 2. The sealing drape 116 and gripping member 120 can work together to form a fluid seal over the patient's wound 102. "Fluid seal," or "seal," means a seal adequate to maintain reduced pressure at a desired site given the particular reduced-pressure source or subsystem involved.

The gripping member 120 may be any material suitable for transmitting the closing force from the contracting elements 118 to the patient's epidermis 104 (which may be deemed to include a gasket or other layer of material) or assist in forming a fluid seal over the wound 102. For example, the gripping member 120 may be a pressure-sensitive adhesive, heat-activated adhesive, sealing tape, double-sided sealing tape, paste, hydrocolloid, hydrogel, hooks, sutures, etc. In the illustrative embodiment, the gripping member 120 is an adhesive layer and spans the width of the second, tissue-facing surface 124 of the sealing drape 116 and overlays the contracting elements 118. It will be appreciated, however, that the gripping member 120 may merely be coupled to tissue-facing surfaces of the drape extensions 126. The gripping member 120 may be formed as a laminar layer or a pattern distributed on the sealing drape 116. Alternatively, in the case of sealing tape, the gripping member 120 may be applied over the entire first surface 122 of the sealing drape 116, or over the first surfaces of the drape extensions 126.

A manifold member 112, or manifold, is positionable between the, second, tissue-facing surface 124 of the sealing drape 116 and at least a portion of the wound 102. The manifold member 112 may be sized to substantially cover the estimated area of the wound 102, although a larger or smaller size may be used in different applications. The manifold member 112 is made from a manifold material.

The term "manifold" as used herein generally refers to a substance or structure that is provided to assist in applying reduced pressure to, delivering fluids to, or removing fluids from the wound 102. The manifold member 112 typically includes a plurality of flow channels or pathways that distribute fluids provided to and removed from the wound 102 around the manifold member 112. In one illustrative embodiment, the flow channels or pathways are interconnected to improve distribution of fluids provided or removed from the wound 102. The manifold member 112 may be a biocompatible material that is capable of being placed in contact with wound 102 and distributing reduced pressure to the wound 102. Examples of manifold members 112 may include, for example, without limitation, devices that have structural elements arranged to form flow channels, such as, for example, cellular foam, open-cell foam, porous tissue collections, liquids, gels, and foams that include, or cure to include, flow channels. The manifold member 112 may be porous and may be made from foam, gauze, felted mat, or any other material suited to a particular biological application.

In one embodiment, the manifold member 112 is a porous foam and includes a plurality of interconnected cells or pores that act as flow channels. The porous foam may be a polyurethane, open-cell, reticulated foam, such as Granu-Foam® material manufactured by Kinetic Concepts, Incorporated of San Antonio, Tex. Other embodiments may include "closed cells." In some situations, the manifold member 112 may also be used to distribute fluids, such as medications, antibacterials, growth factors, and various solutions to the wound 102. Other layers may be included in or on the manifold member 112, such as absorptive materials, wicking materials, hydrophobic materials, and hydrophilic materials. In some instances it may be desirable to add ionic silver to the foam in a microbonding process or to add other substances to the manifold member 112, such as antimicrobial agents. The manifold member 112 may be isotropic or anisotropic depending on the exact orientation of the compressive forces that are desired during reduced pressure. In addition, the manifold material may be a bioabsorbable material.

The manifold member 112 may be coupled to the sealing drape 116. The coupling may occur in many ways. The sealing drape 116 and manifold member 112 may be coupled using adhesives such as an acrylic adhesive, silicone adhesive, hydrogel, hydrocolloid, etc. Alternatively, the sealing drape 116 and manifold member 112 may be bonded by heat bonding, ultrasonic bonding, and radio frequency bonding, etc. The coupling may occur in patterns or more completely. Structure might be added to the bond to make the sealing drape 116 behave anisotropically in a desired direction, i.e., to make an anisotropic drape material. An anisotropic drape material may work in conjunction with the contracting elements 118 to primarily move in a given direction, i.e., only about a certain axis or axes. For example, an anisotropic sealing drape may work in conjunction with the contracting elements to generate a closing force to assist in closing a wound.

The reduced-pressure subsystem 114 includes a reduced-pressure source 132, which can take many different forms. The reduced-pressure source 132 provides a reduced pressure as a part of the reduced-pressure, wound-treatment system 100. The reduced-pressure source 132 provides reduced pressure. The reduced-pressure source 132 may be any device for supplying a reduced pressure, such as a vacuum pump, wall suction, or other source. While the amount and nature of reduced pressure applied to a tissue site or wound will typically vary according to the application, the reduced pressure will typically be between −5 mm Hg and −500 mm Hg and more typically between −100 mm Hg and −300 mm Hg, and still more typically in the range −100 mm Hg and −200 mm Hg.

As used herein, "reduced pressure" generally refers to a pressure less than the ambient pressure at a tissue site or wound that is being subjected to treatment. In most cases, this reduced pressure will be less than the atmospheric pressure at which the patient is located. Alternatively, the reduced pressure may be less than a hydrostatic pressure at the tissue site. Unless otherwise indicated, values of pressure stated herein are gauge pressures. The reduced pressure delivered may be constant or varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure.

In the illustrative embodiment, the reduced-pressure source 132 is shown having a battery compartment 134 and a canister region 136 with windows 138 providing a visual indication of the level of fluid within the canister 136. An interposed membrane filter, such as hydrophobic or oleophobic filter, may be interspersed between a reduced-pressure delivery conduit, or tubing, 140 and the reduced-pressure source 132.

The reduced pressure developed by the reduced-pressure source 132 is delivered through the reduced-pressure delivery conduit 140 to a reduced-pressure interface 142, which may be an elbow port 144. In one illustrative embodiment, the elbow port 144 is a TRAC® technology port available from KCI of San Antonio, Tex. The reduced-pressure interface 142 allows the reduced pressure to be delivered to the wound-closing dressing 110 and realized within an interior portion of wound-closing dressing 110 as well as the manifold member 112. In this illustrative embodiment, the elbow port 144 extends through the sealing drape 116 to the manifold member 112.

One or more devices 141 may be added to the reduced-pressure delivery conduit 140. For example, the device 141 may be a fluid reservoir, or collection member, to hold exudates and other fluids removed. Other examples of devices 141 that may be included on the reduced-pressure delivery conduit 140 or otherwise fluidly coupled to the reduced-pressure delivery conduit 140 include the following non-limiting examples: a pressure-feedback device, a volume detection system, a blood detection system, an infection detection system, a flow monitoring system, a temperature monitoring system, etc. Some of these devices may be formed integral to the reduced-pressure source 132.

In operation, the reduced-pressure, wound-treatment system 100 may be applied to the wound 102 of the patient. The manifold member 112 is first placed over the wound 102. The manifold member 112 may be placed within the wound 102 or may overlay a portion of the wound 102. If the wound-closing dressing 110 has not been coupled to the manifold member 112, the wound-closing dressing 110 may then be placed over the top of the manifold member 112 such that drape extensions 126 of the sealing drape 116 extend beyond the periphery of the wound 102. The drape extensions 126 are secured to the patient's epidermis 104 by the gripping member 120 in order to form a fluid seal over the wound 102. The one or more contracting elements 118 may then be activated such that the contracting elements 118 generate a contracting force (shown by arrows 128) that is transmitted to the patient's epidermis 104 via the gripping member 120 so that wound edges 101 are drawn closer together.

The reduced-pressure interface 142 is applied, if not already installed, and the reduced-pressure delivery conduit 140 fluidly coupled at one end. The other end of the reduced-pressure delivery conduit 140 is fluidly coupled to the reduced-pressure source 132. The reduced-pressure source 132 may then be activated such that reduced pressure is delivered to the wound-closing dressing 110. Advantageously, if the contracting elements 118 are activated by moisture from a fluid, as discussed previously, application of reduced pressure may, in part, serve to draw the extra fluid out from the interior of the wound-closing dressing 110 and onto the contracting elements 118.

As the pressure is reduced, the manifold member 112 compresses and contracts laterally to form a semi-rigid substrate. The reduced pressure is transmitted further still through the manifold member 112 so that the reduced pressure is experienced at the patient's epidermis 104 and at the wound 102. The reduced pressure delivered to the manifold member 112 may develop a compressive force 146 that may provide stability and therapy. The compressive force 146 may be more than just at the top of the epidermis 104; the compressive force 146 may extend down deeper and may be experienced at the level of subcutaneous tissue 108.

As the sealing drape 116 and manifold member 112 laterally contract under the influence of the reduced pressure, and as the downward force acts through the Poisson's ratio for the epidermis 104, an inward force 148 may develop that may help hold an additional closing force on the wound 102 and may generally provide additional stability to the wound 102. Thus, the inward force 148 from the reduced pressure and the force 130 from the contracting elements 118 may act together to assist in closing the wound 102. At the same time, the reduced pressure delivered to and through the manifold member 112 helps to remove any exudates and other fluids from the wound 102 and provides reduced pressure therapy to the wound 102. All of these actions may improve healing of the wound 102.

Figure 3B:
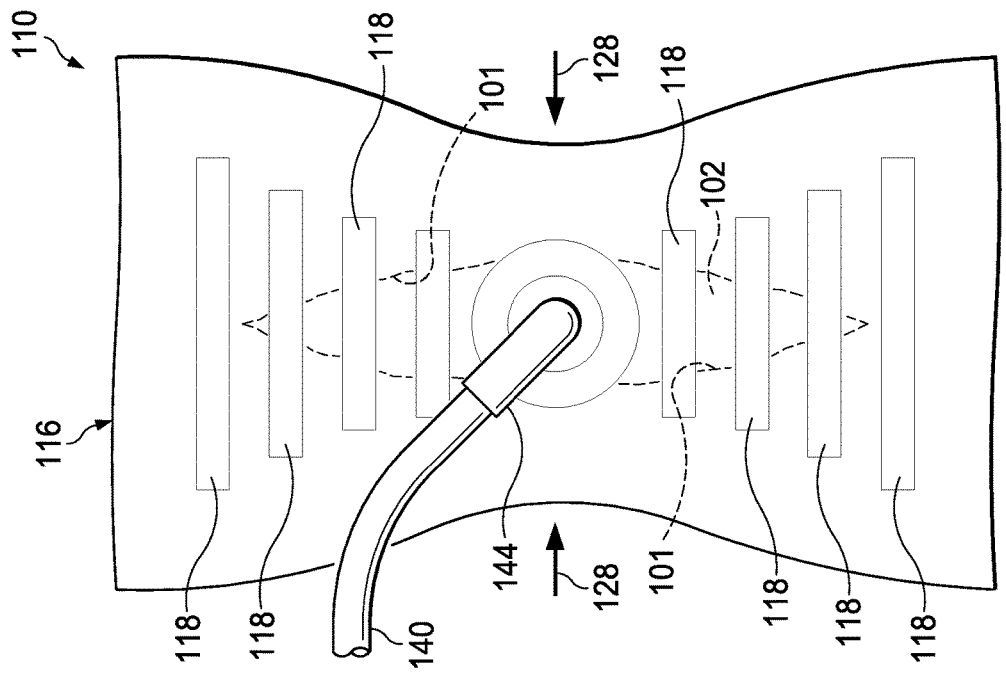
FIG. 3B is a schematic, top view of the system of FIG. 1 showing several contracting elements activated thereby generating a closing force.
Figure 3A:
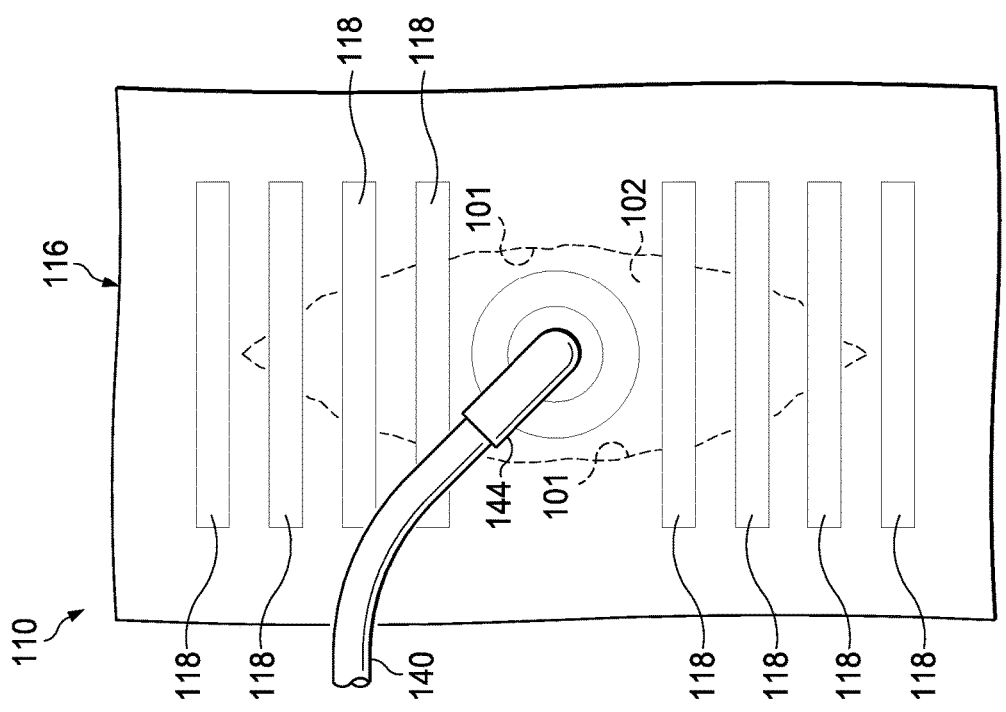
FIG. 3A is a schematic, top view of the system of FIG. 1.

Referring to FIG. 3A, the wound-closing dressing 110 is shown deployed on a wound 102 before the activation of the contracting elements 118. FIG. 3B shows the wound-closing dressing 110 after at least the three most inboard contracting elements 118 have contracted at least in part to provide a closing force as suggested by arrows 128.

It may be desirable to apply the reduced-pressure, wound-treatment system 100 in the operating room and allow the reduced-pressure, wound-treatment system 100 to remain on the patient until adequate healing has taken place. In this regard, it may be desirable to form the sealing drape 116, manifold member 112, and any other layers from transparent materials to allow the healthcare provider to gain visual cues about the healing of the wound 102 without having to remove the wound-closing dressing 110. Moreover, it should be appreciated that the reduced-pressure, wound-treatment system 100 may be used as a primary wound-closing treatment or as an intermediate step of a wound-closing treatment. Furthermore, it will be appreciated that the wound-closing dressing 110 may be used without the manifold member 112 or reduced-pressure subsystem 114. The wound-closing dressing 110 may be beneficial as a stand-alone bandage that is capable of delivering a closing force to a wound 102 without requiring reduced pressure.

Figure 4A:
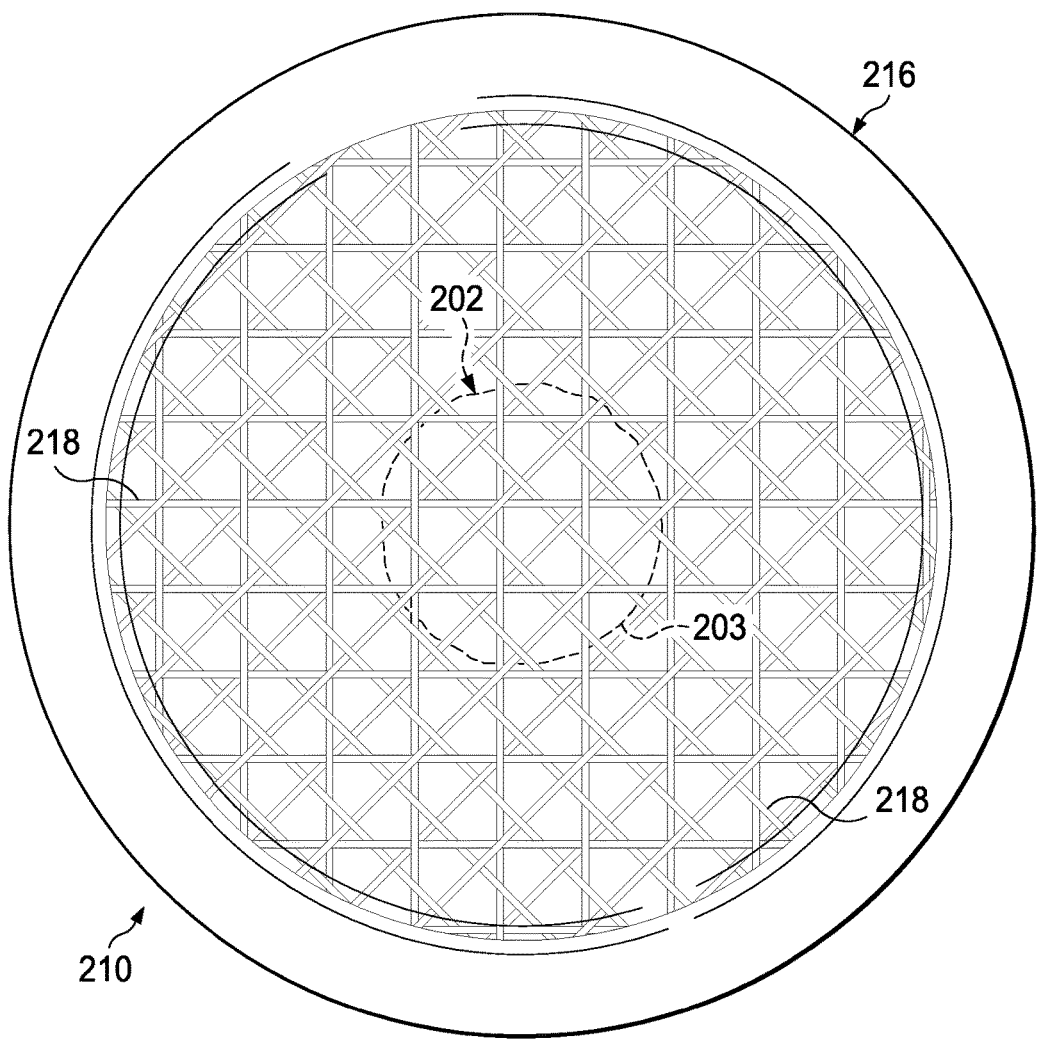
FIG. 4A is a schematic, top view of an illustrative, non-limiting embodiment of a wound-closing dressing shown over a wound.
Figure 4B:
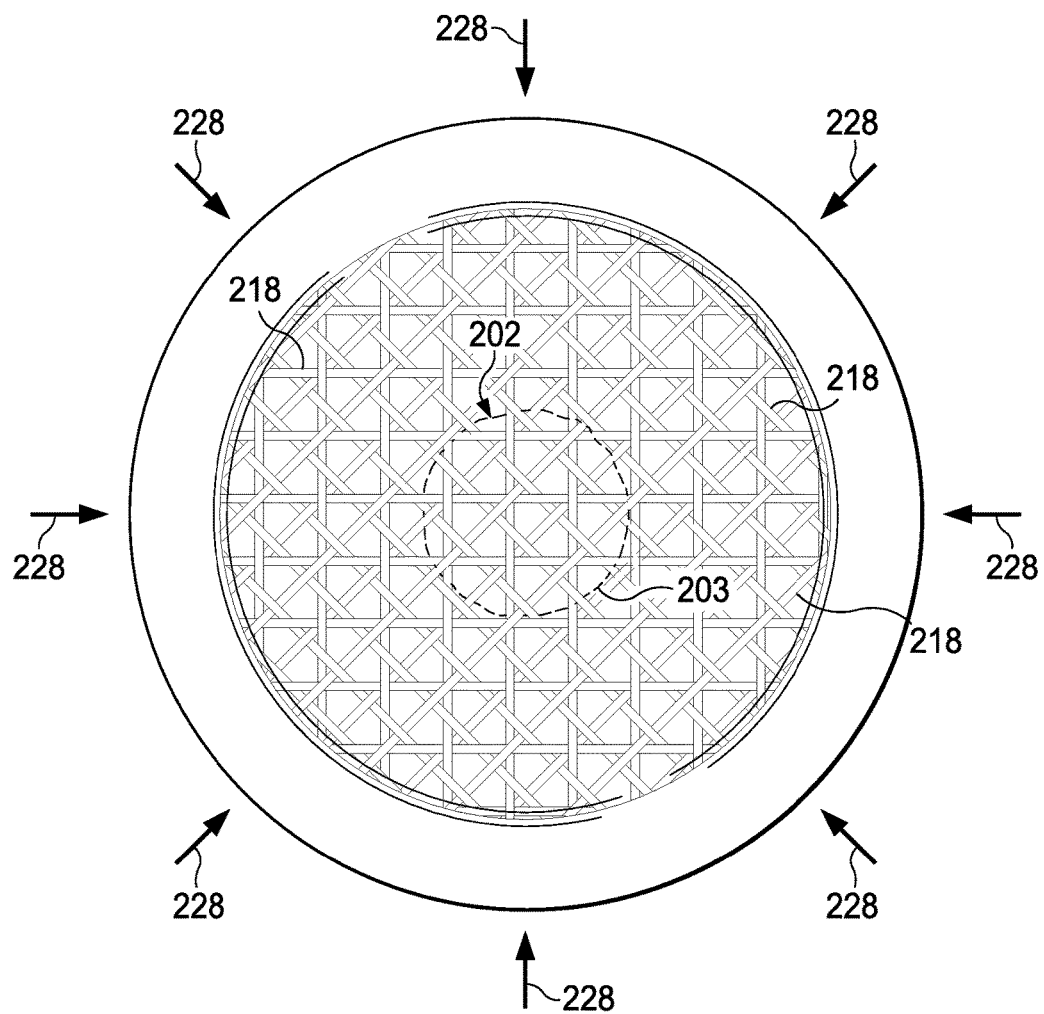
FIG. 4B is a schematic, top view of the dressing of FIG. 4A showing the contracting element activated thereby generating a closing force.

Referring now primarily to FIGS. 4A and 4B, an illustrative embodiment of a wound-closing dressing 210 is shown. The wound-closing dressing 210 is analogous in most respects to the wound-closing dressing 110 and related components of FIGS. 1-3B and a correlation of parts is generally indicated in this embodiment by indexing the numerals by 100. For example, sealing drape 216 is analogous to sealing drape 116. While presented as a separate wound-closing dressing, the wound-closing dressing 210 could be used as part of a reduced-pressure system, such as the reduced-pressure, wound-treatment system 100. The wound-closing dressing 210 may be shaped to approximate the shape of a wound 202 or extend beyond the wound 202. While the plan view of wound-closing dressing 210 is shown as substantially circular, it will be appreciated that the wound-closing dressing 210 may have any suitable plan view, including, but not limited to, square, rectangular, triangular, elliptical, hexagonal, octagonal, irregular, etc. The contracting elements 218 may be woven together in a "thatched" pattern such that, when activated, a substantially equal closing force (represented by arrows 228 in FIG. 4B) may be distributed about an entire periphery 203 of the wound 202. FIG. 4A shows the wound-closing dressing 210 and wound 202 prior to activation of the contracting elements 218, and FIG. 4B shows the wound-closing dressing 210 and wound 202 after the contracting elements 218 have been activated.

Figure 5:
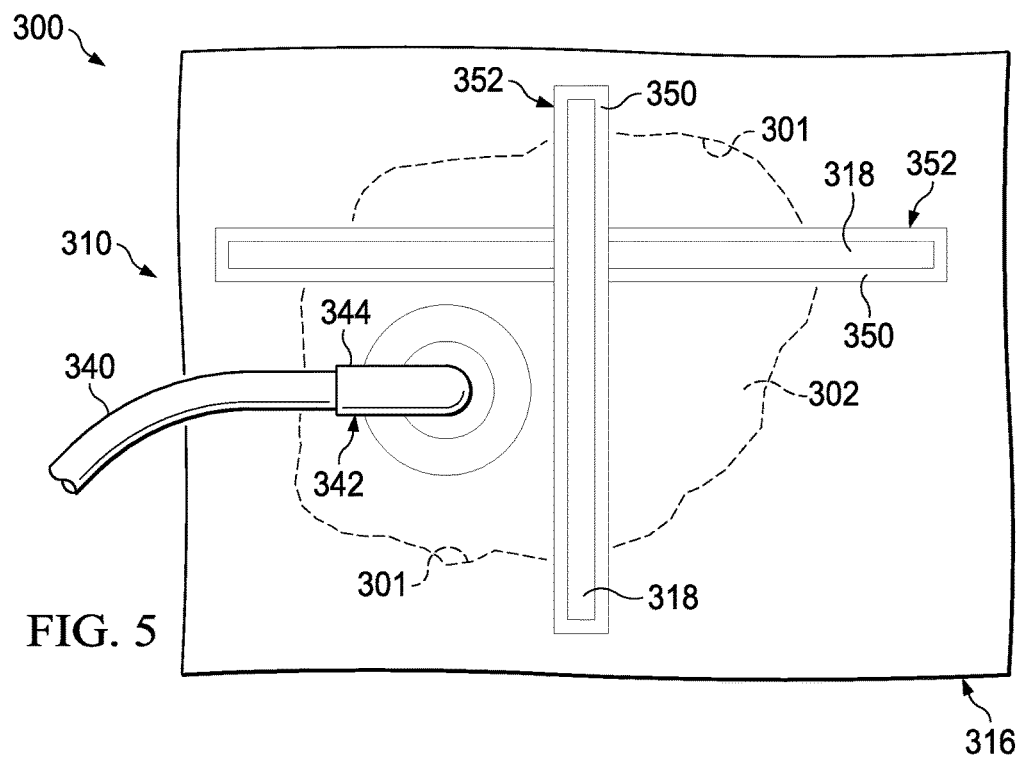
FIG. 5 is a schematic, top view of an illustrative, non-limiting embodiment of a system for treating a wound.

Referring now primarily to FIG. 5, another illustrative reduced-pressure, wound-closure system 300 for treating a wound 302 on a patient is shown. The system is generally analogous in most respects to that of the reduced-pressure, wound-treatment system 100 of FIGS. 1-3B. Analogous parts are indicated by indexing the reference numerals of FIGS. 1-3B by 200. In this illustrative embodiment, a plurality of contracting elements 318 and backing strips 350 may be utilized. Each contracting element 318 and corresponding backing strip 350 form a contracting strip 352. Hence a plurality of contracting strips 352 may be utilized. Each contracting element 318 is releasably coupled to the corresponding backing strip 350. As before, the contracting element 318 is configured to contract when activated in order to generate a closing force that may assist in closing the wound 302. The contracting elements 318 may be releasably coupled to the backing strip 350 in a stretched position or may be moved to a stretched position as the contracting strip 352 is applied to the patient. In either case, when the contracting element 318 is activated, the contracting element 318 seeks to return to a non-stretched position, or free position, and thereby contracts to generate a closing force.

While the illustrative embodiment shows each contracting strip 352 as having a single contracting element 318, it will be appreciated that any suitable number of contracting elements 318 may be employed. Furthermore, in the event that the contracting strip 352 includes a plurality of contracting elements 318, the plurality of contracting elements 318 may be arranged in any suitable pattern relative to one another, e.g., parallel, perpendicular, angled, etc. While a plurality of contracting elements 318, backing strips 350, and contracting strips 352 are mentioned, single members of each may be used as well. As with other embodiments, the contracting element 318 may be formed from any suitable material that contracts in response to being activated and may be activated in numerous ways.

The backing strips 350 may be formed from any suitable material including, but not limited to, gauze, an elastomer, an adhesive, etc. Any suitable number of contracting strips 352 may be placed over the wound 302 and a manifold member, e.g., the manifold member 112 in FIG. 2. Each contracting strip 352 may be secured to epidermis by corresponding gripping members in any suitable pattern to assist in closing the wound 302. A sealing drape 316 having a reduced-pressure interface 342 may be placed over the contracting strips 352 such that a reduced pressure may be delivered to the wound 302; alternatively or in addition, the contracting strips 352 may be placed atop the sealing drape 316. In an alternative embodiment, the backing strip 350 of each contracting strip 352 employed may be formed from a drape material whereby each backing strip 350 works together with one or more adjacent backing strips 350 so as to form an unified drape thereby eliminating the need for an additional sealing drape; in this embodiment, it may be desirable to use a gripping member (e.g., an adhesive) having a high Moisture Vapor Transfer Rate (MVTR). In yet another alternative embodiment, the contracting strips 352 may be used as stand-alone components (e.g., without the manifold and reduced pressure subsystem) to assist in closing a wound.

Figure 6:
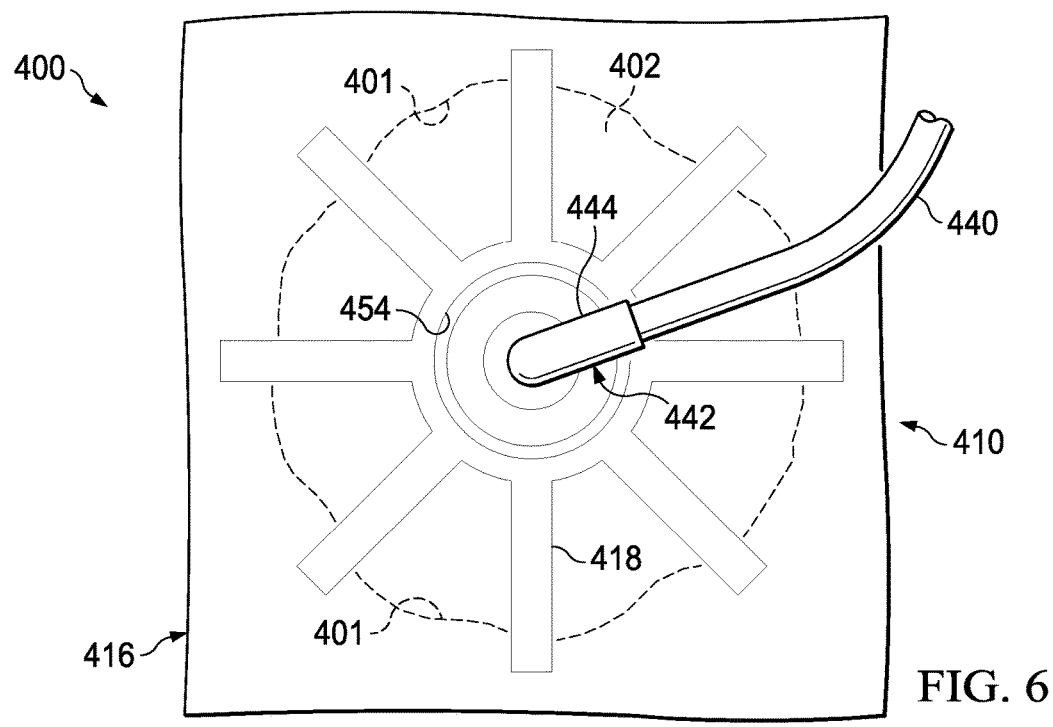
FIG. 6 is a schematic, top view of an illustrative, non-limiting embodiment of a system for treating a wound shown.

Referring now primarily to FIG. 6, another illustrative, non-limiting embodiment of a reduced-pressure, wound-closure system 400 for treating a wound 402 is presented. The reduced-pressure, wound-closure system 400 is generally analogous in most respects to that of the reduced-pressure, wound-treatment system 100 of FIGS. 1-3B and analogous parts are indicated by indexing the reference numerals of FIG. 1-3B by 300. Contracting elements 418 are arranged in a "star-shaped" pattern to deliver substantially equal closing forces to a periphery 401 of a wound 402. The contracting elements 418 include a central aperture 454 for receiving a reduced-pressure interface 442 therethrough. While the illustrative contracting elements 418 are shown as having eight "legs", it will be appreciated that the contracting elements 418 may include any suitable number of legs and may be made as an integrated unit as shown or by a plurality of components.

Figure 7A:
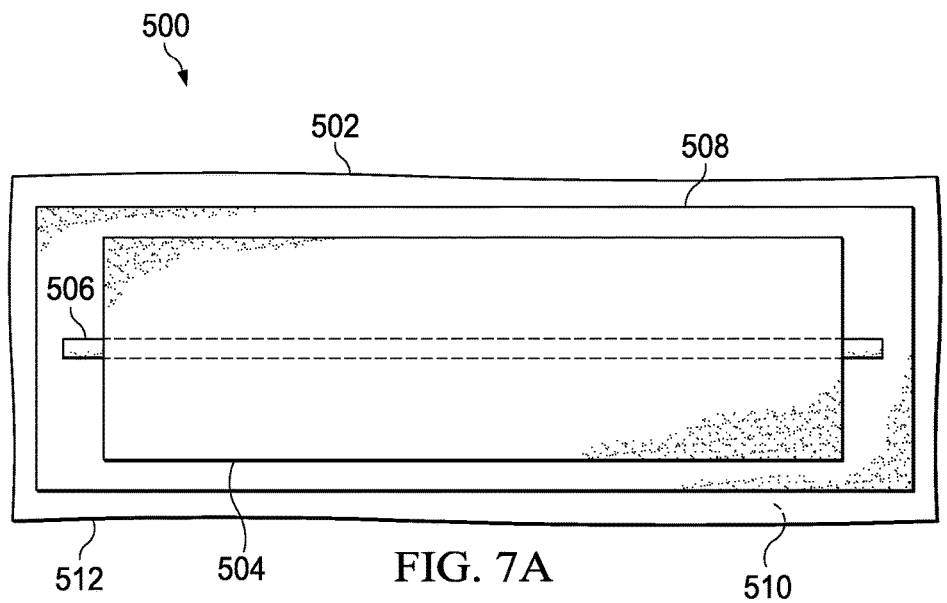
FIG. 7A is a schematic, bottom view of a portion of an illustrative, non-limiting embodiment of a system for treating a wound.
Figure 7B:
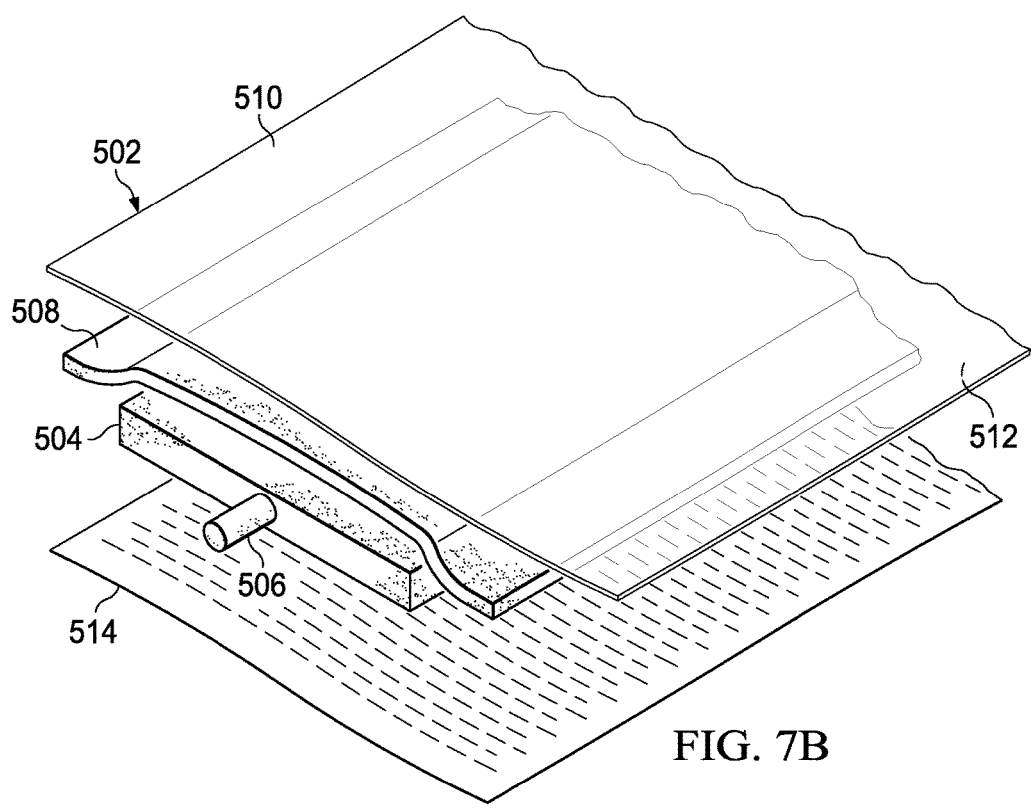
FIG. 7B is a schematic, perspective view of the system of FIG. 7A.

Reference is now made primarily to FIG. 7A, which is a schematic bottom view of a portion of an illustrative embodiment of a system for treating a wound, and FIG. 7B. These figures include an alternative embodiment of a wound-closing dressing 500 for closing a wound. The wound-closing dressing 500 includes a sealing drape 502, a dissolvable body 504, an elastic member 506, and a gripping member 508. The wound-closing dressing 500 may be used as a stand-alone component to assist in wound closure or may be used as part of a reduced-pressure system to assist in wound closure and treatment. The sealing drape 502 includes a first surface 510 and a second, tissue-facing surface 512. The sealing drape 502 generally may be formed from the same or similar materials to that of the sealing drape 116 of FIGS. 1-3B and may operate in a like manner. Optionally, the sealing drape 502 may be fenestrated to permit moisture to pass from the first surface 510 to the dissolvable body 504.

The dissolvable body 504 is coupled to the second, tissue-facing surface 512 of the sealing drape 502. The dissolvable body 504 may be formed from any suitable dissolvable material, including, but not limited to, biodegradable or bioabsorbable materials, such as polylactide (PLA), poly(lactic-co-glycolic acid) (PLGA), polyglycolide (PGA), polycaprolactone (PCL), sodium chloride, or the like. Additionally, the dissolvable body 504 may include oxygenated particles or anti-microbial particles for reducing infection. The dissolvable body 504, which holds the elastic member 506 in a stretched position, may dissolve under the influence of any suitable factor, including, but not limited to, moisture, heat, ultrasound, etc. When the dissolvable body 504 dissolves, the elastic member 506 is, at least partially, released thereby generating a closing force as the elastic member 506 seeks to return to an unstretched position. While the illustrative embodiment shows a single dissolvable body 504, it will be appreciated that any suitable number of dissolvable bodies may be employed (see e.g., FIGS. 8-9B).

The elastic member 506 is coupled to the dissolvable body 504 in a stretched position such that when the dissolvable body 504, or a portion thereof, dissolves, the elastic member 506 contracts to generate a closing force. The elastic member 506 may be coupled to the dissolvable body 504 by any suitable device or technique, including, but not limited to adhesive, mechanical fasteners, bonding, sonic welding, etc. Alternatively or in addition, the elastic member 506 may be coupled by embedding the elastic member 506 in the dissolvable body 504. The elastic member 506 may be any suitable material that is capable of being coupled to the dissolvable body 504 in a stretched position and capable of contracting when at least a portion of the dissolvable body 504 dissolves. For example and without limitation, the elastic member 506 may be formed from an elastomer. As used herein, the term "coupled" includes coupling via a separate object and includes direct coupling. The term "coupled" also encompasses two or more components that are continuous with one another by virtue of each of the components being formed from the same piece of material. Also, the term "coupled" may include chemical, such as via a chemical bond, mechanical, thermal, or electrical coupling. Coupling may further include embedding one member in another.

As clearly shown in FIG. 7B, the elastic member 506 in this illustrative embodiment has a substantially circular cross-section. It will be appreciated, however, that the elastic member 506 may have any suitable cross-section. Moreover, it will be appreciated that the elastic member 506 may have any suitable configuration. For example, the elastic member 506 may be arranged in a "thatched" pattern, a cross pattern, parallel pattern, etc. Also, while the illustrative embodiment shows a single elastic member 506, it will be appreciated that any suitable number of elastic members 506 may be coupled to the dissolvable body 504 or bodies 504. Also, the ends of the elastic member 506 may be coupled to the sealing drape 502 such that the contracting force generated by the elastic member 506 may be directly transferred to the gripping member 508 (as discussed further below).

The gripping member 508 is the same or similar to that of the gripping member 120 in the reduced-pressure, wound-treatment system 100 of FIGS. 1-3B. The gripping member 508 may be coupled to at least one of the sealing drape 502, dissolvable body 504, or elastic member 506. The gripping member 508 is configured to transfer the force generated by the contracting of the elastic member 506 to the patient's epidermis to assist in closing a wound. Optionally, as best shown in FIG. 7B, the wound-closing dressing 500 may also include a fenestrated sheet 514 that is disposed between the dissolvable body 504 and the wound in order to regulate the amount of moisture from the patient's exudate that is permitted to pass to the dissolvable body 504. This may be useful to control the amount or rate that the dissolvable body 504 dissolves in instances where the dissolvable body 504 dissolves when moisture is introduced thereto.

Figure 8:
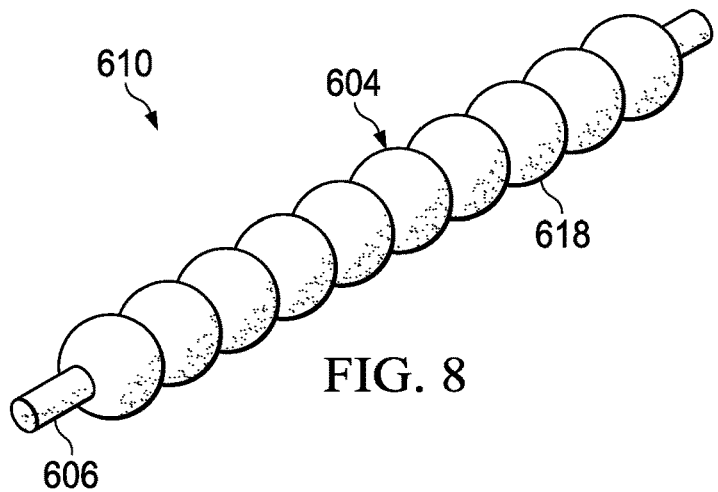
FIG. 8 is a schematic, perspective view of a portion of an illustrative, non-limiting embodiment of a system for treating a wound.
Figure 9A:
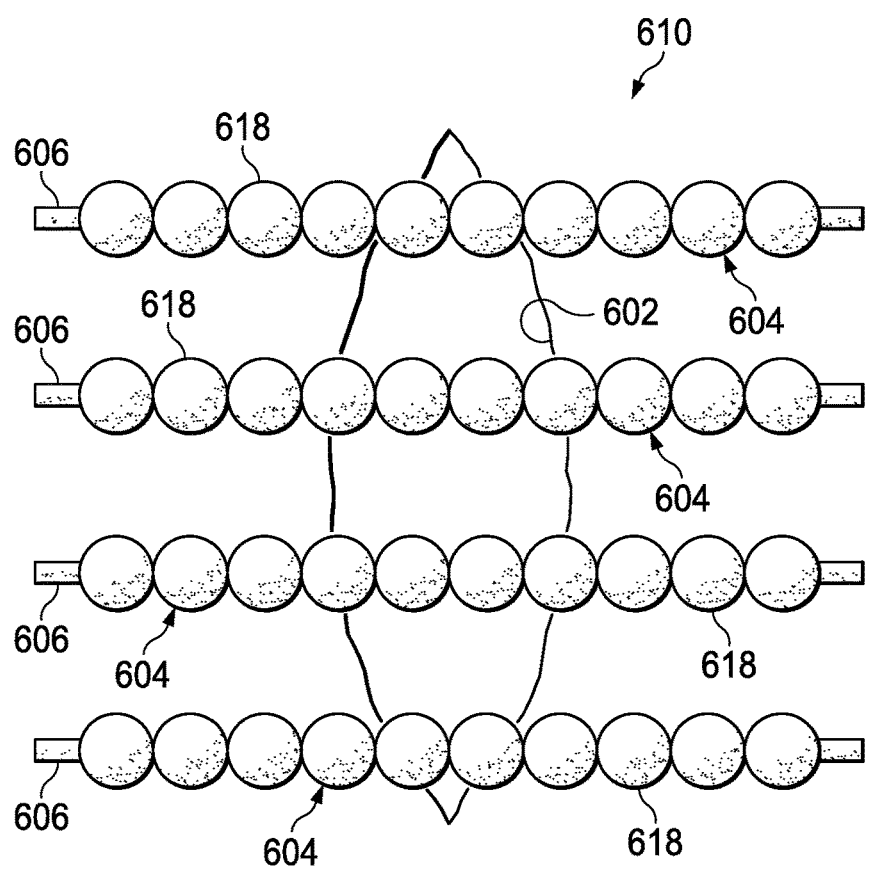
FIG. 9A is a schematic, top view of the system portion of FIG. 8.
Figure 9B:
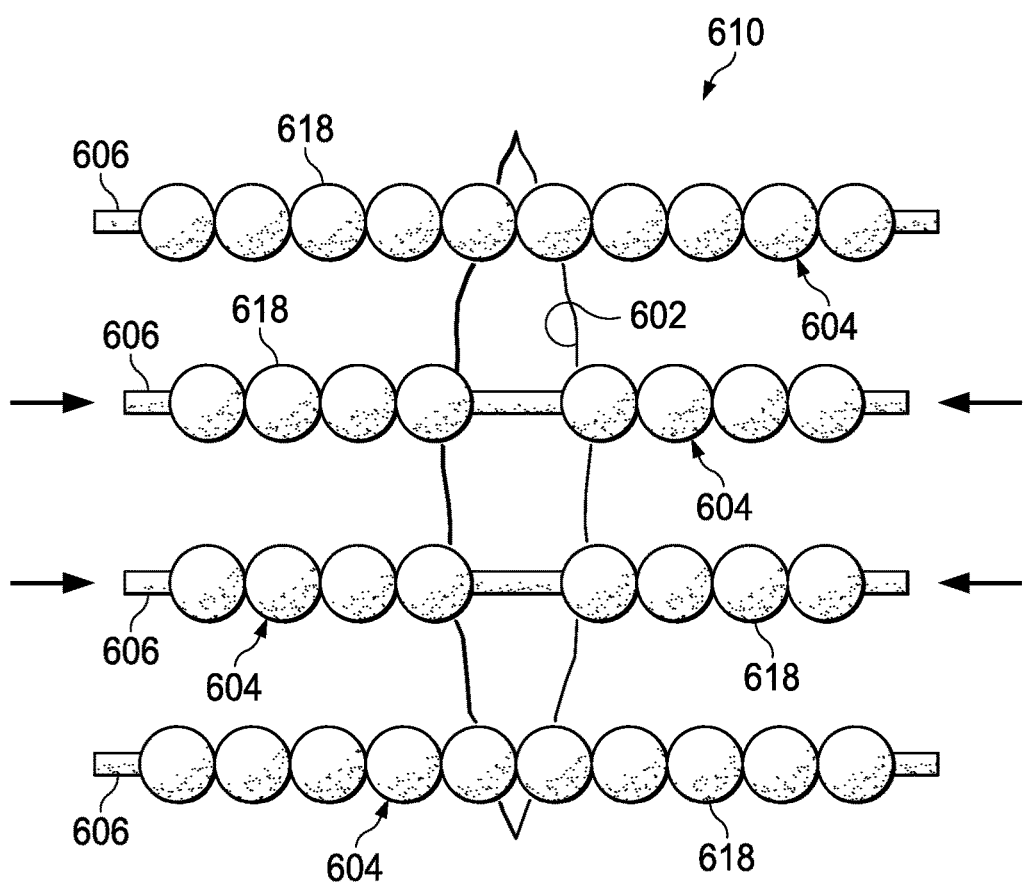
FIG. 9B is a schematic, top view of the system portion of FIG. 8 showing several beads dissolved whereby the corresponding elastic members generate a closing force.

Referring now primarily to FIGS. 8-9B, another wound-closing dressing 610 for treating a wound 602 is shown. The wound-closing dressing 610 is generally analogous in most respects to that of the wound-closingdressing 500 of FIGS. 7A and 7B. Analogous parts are indicated by indexing the reference numerals of FIGS. 7A and 7B by 100. In this embodiment, a dissolvable body 604 includes a plurality of dissolvable beads 618 or other dissolvable members. The plurality of dissolvable beads 618 hold the force generated by a stretched elastic member 606, and so as the plurality of dissolvable beads 618 are dissolved, an increasing force is experienced by a gripping member (not shown) that is attached to the elastic member 606. The beads 618 are typically dissolved by exudate from the wound 602. When a bead 618 dissolves, the contracting force generated by the corresponding elastic member 606 increases. The generated closing force may have a direct relationship to the number of beads 618 that are dissolved. For example, as the number of beads 618 dissolved increases, the generated closing force may increase with a defined relationship, e.g., linearly, exponentially, etc.

Thus, as clearly shown in FIGS. 9A and 9B, the wound-closing dressing 610 may be "tuned" to generate a greater closing force at the wider portions of the wound 602. Moreover, this may occur in a self-regulating way. In other words, areas of the wound 602 that have increased levels of exudate, typically the wider portions of the wound 602, experience a greater closing force because the increased levels of exudate cause more beads 618 to dissolve which increases the closing force generated by the elastic member 606. The wound-closing dressing 610 may be used in conjunction with a sealing drape and gripping member similar to those of the wound-closing dressing 510 of FIGS. 7A and 7B and as part of a reduced-pressure treatment system. Alternatively, each end of each elastic member 606 may be secured to the patient's epidermis and the wound-closing dressing 610 used as a stand-alone dressing for assisting in wound closure.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in a connection to any one embodiment may also be applicable to any other embodiment.

What is claimed:

1. A method for treating a wound, comprising: securing a contracting element formed in an extended position to an epidermis such that the contracting element spans at least a portion of the wound, wherein the contracting element is configured to move from the extended position to a contracted position in response to being activated; and activating the contracting element to move the contracting element to the contracted position and generate a closing force on the wound,
    wherein the contracting element comprises a material stretched from a free length to a stretched length and dried and wherein the contracting element is activated by moisture.

2. The method according to claim 1 wherein said contracting element comprises a plurality of contracting strips.

3. The method according to claim 1 wherein securing the contracting element comprises coupling the contracting element to a gripping member.

4. The method according to claim 1, further comprising coupling a dissolvable body to the contracting element, and wherein the contracting element is activated when at least a portion of the dissolvable body dissolves.

5. The method according to claim 1, further comprising coupling a dissolvable body to the contracting element, wherein the contracting element is activated when at least a portion of the body dissolves; and wherein the dissolvable body comprises a plurality of dissolvable beads.

6. The method according to claim 1 wherein said contracting element is coupled to a tissue-facing surface of a sealing drape.

7. The method according to claim 1 further comprising applying a reduced pressure to the wound.

8. The method according to claim 4, wherein the dissolvable body includes oxygenated particles for reducing infection.

9. The method according to claim 4, wherein the dissolvable body includes anti-microbial particles for reducing infection.

10. A method for treating a wound, comprising:
   securing a dissolvable body across the wound; and
   coupling a contracting element to the dissolvable body, wherein the contracting element is configured to contract from an extended position to a contracted position when at least a portion of the dissolvable body dissolves.

11. The method of claim 10, further comprising coupling a gripping member to at least one of the dissolvable body and contracting element, the gripping member configured to transmit a closing force to an epidermis adjacent to the wound.

12. The method of claim 11, wherein the gripping member is fenestrated.

13. The method of claim 10, wherein the dissolvable body comprises a plurality of dissolvable beads.

14. The method of claim 10, wherein the dissolvable body includes oxygenated particles for reducing infection.

15. The method of claim 10, wherein the dissolvable body includes anti-microbial particles for reducing infection.

16. The method of claim 10, wherein the dissolvable body comprises a sheet.

\* \* \* \* \*